United States Patent
Cerrone et al.

(10) Patent No.: US 11,376,542 B2
(45) Date of Patent: Jul. 5, 2022

(54) APPARATUS AND METHOD FOR TREATMENT OF PROCESS VAPOURS COMING FROM A VACUUM CONCENTRATION SECTION OF A UREA PLANT

(71) Applicant: SAIPEM S.p.A., San Donato Milanese (IT)

(72) Inventors: Cristina Cerrone, San Donato Milanese (IT); Jacopo Cedrati, San Donato Milanese (IT)

(73) Assignee: SAIPEM S.P.A., San Donato Milanese (IT)

( * ) Notice: Subject to any disclaimer, the term of this patent is extended or adjusted under 35 U.S.C. 154(b) by 177 days.

(21) Appl. No.: 16/652,607

(22) PCT Filed: Oct. 25, 2018

(86) PCT No.: PCT/IB2018/058337
§ 371 (c)(1),
(2) Date: Mar. 31, 2020

(87) PCT Pub. No.: WO2019/082121
PCT Pub. Date: May 2, 2019

(65) Prior Publication Data
US 2020/0254377 A1 Aug. 13, 2020

(30) Foreign Application Priority Data
Oct. 25, 2017 (IT) .................. 102017000121364

(51) Int. Cl.
*B01D 53/00* (2006.01)
*C07C 273/16* (2006.01)
(Continued)

(52) U.S. Cl.
CPC ............. *B01D 53/002* (2013.01); *B01D 3/10* (2013.01); *B01D 53/1406* (2013.01);
(Continued)

(58) Field of Classification Search
USPC .................... 203/42; 95/232; 202/172, 185.2
See application file for complete search history.

(56) References Cited

U.S. PATENT DOCUMENTS 2,682,499 A 6/1954 Thurman
3,985,523 A 10/1976 Kaupas et al.
(Continued)

FOREIGN PATENT DOCUMENTS

| | | |
|---|---|---|
| CN | 1980887 A | 6/2007 |
| EP | 0 302 213 | 2/1989 |
| WO | WO2008141784 A2 | 11/2008 |

OTHER PUBLICATIONS

Chinese Office Action and Search Report for Application No. 201880063770.7 dated May 31, 2021 (7 pages).
(Continued)

*Primary Examiner* — Nina Bhat
(74) *Attorney, Agent, or Firm* — Neal, Gerber & Eisenberg LLP (57) ABSTRACT

An apparatus for treatment of process vapours coming from a vacuum concentration section of a urea plant, comprising a vacuum system having a plurality of successive condensation stages, connected in series by respective line portions and crossed in series by process vapours to be treated; the apparatus has at least one primary steam condensate inlet for feeding steam condensate to the vacuum system and positioned, with reference to a circulation direction of the process vapours in the vacuum system, upstream of at least one selected condensation stage, or in at least one selected condensation stage.

24 Claims, 5 Drawing Sheets

(51) Int. Cl.
*B01D 3/10* (2006.01)
*B01D 53/14* (2006.01)

(52) U.S. Cl.
CPC ...... *C07C 273/16* (2013.01); *B01D 2252/103* (2013.01); *B01D 2257/406* (2013.01)

(56) References Cited

U.S. PATENT DOCUMENTS

| | | | |
|---|---|---|---|
| 4,003,801 A | | 1/1977 | Chikaoka et al. |
| 4,256,662 A | * | 3/1981 | Gorlovsky ............ C07C 273/04 564/67 |
| 5,276,183 A | * | 1/1994 | Pagani ................. C07C 273/04 564/67 |
| 5,744,009 A | * | 4/1998 | Singh .................... C07C 273/16 203/42 |
| 6,623,546 B1 | * | 9/2003 | Bourdel ................ F26B 25/006 95/199 |
| 6,723,876 B2 | * | 4/2004 | Speth ....................... C01B 3/025 423/59 |
| 8,129,565 B2 | * | 3/2012 | Zardi .................... C07C 273/04 564/67 |
| 10,501,407 B2 | * | 12/2019 | Baharuddin ......... B01J 19/2415 |
| 10,919,846 B2 | * | 2/2021 | Patil ....................... B01D 3/009 |
| 2002/0082451 A1 | * | 6/2002 | Yoshida ................ C07C 273/04 564/70 |
| 2002/0088243 A1 | * | 7/2002 | Holtzapple ............... F24F 5/00 62/268 |
| 2005/0038293 A1 | * | 2/2005 | Jonckers ............... C07C 273/04 564/67 |
| 2005/0065374 A1 | * | 3/2005 | Pennino ............... B01D 5/0012 564/66 |
| 2008/0242890 A1 | * | 10/2008 | Zardi .................... C07C 273/04 564/67 |

OTHER PUBLICATIONS

Notification Concerning Submission, Obtention or Transmittal of Priority Document for International Application No. PCT/IB2018/058337 dated Jan. 30, 2019.
International Search Report and Written Opinion for International Application No. PCT/IB2018/058337 dated Dec. 17, 2018.
PCT Demand for International Preliminary Examination and Reply to International Search Report and the associated Written Opinion for International Application No. PCT/IB2018/058337 dated Aug. 21, 2019.
Notification of Receipt of Demand by Competent International Preliminary Examining Authority (Form PCT/IPEA/402) for International Application No. PCT/IB2018/058337 dated Sep. 11, 2019.
Second Written Opinion for International Application No. PCT/IB2018/058337 dated Nov. 14, 2019.
Reply to the Second Written Opinion for International Application No. PCT/IB2018/058337 dated Jan. 14, 2020.
Notification of Transmittal of the International Preliminary Report on Patentability (Form PCT/IPEA/416) for International Application No. PCT/IB2018/058337 dated Feb. 4, 2020.

* cited by examiner

APPARATUS AND METHOD FOR TREATMENT OF PROCESS VAPOURS COMING FROM A VACUUM CONCENTRATION SECTION OF A UREA PLANT

PRIORITY CLAIM

This application is a national stage application of PCT/IB2018/058337, filed on Oct. 25, 2018, which claims the benefit of and priority to Italian Patent Application No. 102017000121364, filed on Oct. 25, 2017, the entire contents of which are each incorporated by reference herein.

TECHNICAL FIELD

The present disclosure relates to an apparatus and a method for the treatment of process vapours coming from a vacuum concentration section of a urea plant.

BACKGROUND

As is known, urea is produced on an industrial scale via processes based on the reaction, under relatively high-temperature and relatively high-pressure conditions, between carbon dioxide and ammonia to form ammonium carbamate (intermediate), and the subsequent decomposition reaction of ammonium carbamate to provide urea and water.

The overall synthesis reaction is an equilibrium reaction adversely affected by excess water; as it is an equilibrium reaction, it is necessary to separate the reaction product from the intermediate and from the unconverted reagents.

In general, the urea synthesis reaction is carried out in a reactor from which an aqueous urea solution is obtained that is then progressively concentrated, with the recovery and recycling of unconverted reagents, and solidified in a finishing section (for example, in a granulator or prilling tower).

For example, in the traditional urea process/plant known as "Snamprogetti", the synthesis and successive decomposition and separation take place in the following sections:
  relatively high-pressure synthesis, decomposition and recovery section;
  relatively medium-pressure decomposition and recovery section;
  relatively low-pressure decomposition and recovery section;
  vacuum evaporation and concentration section;
  water treatment section (process condensates);
  finishing section (prilling or granulation).

The vacuum evaporation and concentration section (also referred to simply as the vacuum concentration section or vacuum section) is usually fed with a urea solution containing 70-85% urea by weight, 2-3% ammonia by weight, and approximately 0.5% carbon dioxide by weight: the remaining part is constituted by water produced in the synthesis reaction.

Depending on the type of finishing required for the product (granulated or prilled urea), the vacuum concentration is normally performed in one or two concentration stages, each normally having a concentrator and a separator associated with a vacuum system. The main function of the vacuum system is to ensure the necessary operating pressure of the upstream concentration stage by the condensation of the vapours coming therefrom. Pressure control is critical, because it determines the amount of water in the final product and consequently its quality.

In the case of granulated urea production, it is necessary to achieve a urea solution concentration of around 96-97% by weight, corresponding to an operating pressure in the concentration section of approximately 0.3 kg/cm2(a): a single concentration stage is generally sufficient to ensure the required operating conditions.

In the case of prilled urea production, in addition to the concentration stage operating at approximately 0.3 kg/cm2(a), a second concentration stage operating at approximately 0.03 kg/cm2(a) is necessary to obtain a urea solution concentration of 99.7-99.8% by weight: in this case, two vacuum systems are necessary to ensure the required operating conditions.

In all cases, operating below atmospheric pressure entails a certain amount of air being taken in (through the flanges, porousness of the metal, any manufacturing defects of the equipment, etc.) in addition to the air introduced into the system by instrumentation flushing and the air used for pressure control in the upstream sections. The amount of incoming air is proportional to the vacuum level and the volumes of the equipment operating in a vacuum.

Typically, the concentrations of ammonia and air entering the first vacuum system are approximately 7-10% by weight and 0.1-0.2% by weight, respectively; and the concentrations of ammonia and air entering the second vacuum system are approximately 0.4-0.6% by weight and 0.7-1% by weight, respectively.

The presence of air adversely affects the condensation of the vapours coming from the upstream equipment and must therefore be purged from the system. In the purge current there is a certain amount of ammonia (generally ranging between approximately 12000 mg/Nm3 and 26000 mg/Nm3, depending on the type of product finishing) that must be reduced, both for possible environmental problems and because ammonia is a raw material for the production of urea.

In a typical vacuum system according to certain of the known art, the condensation of process vapours is performed in successive condensation stages of increasing pressure. Basically, a vacuum system of this type comprises a plurality of condensers (heat exchangers) defining respective condensation stages, connected in series and operating at increasing pressure; the increase in pressure between two successive stages is usually obtained through steam ejectors; the process vapours pass through the condensation stages in series. Cooling water is fed to the last condensation stage and then in series to each of the preceding condensation stages (normally excluding the first condensation stage). In each condensation stage, a process condensate is separated, which is collected and transferred to the water treatment section to recover the reagents, and a flow of uncondensed vapours passes to the next condensation stage. The incondensable purge gases leaving the last condensation stage are washed with a steam condensate in order to limit the ammonia content.

The process vapours that condense in the various condensation stages, together with all the steam condensate (both that resulting from the condensation of steam used as the motive fluid in the ejectors, and that used for the final washing), constitute the process condensate, which is normally collected in an atmospheric tank by barometer tubes and then transferred to the water treatment section for recovery of the reagents and their recycling to the synthesis section.

With the typical vacuum system layout just described, the greater the amount of air in the system, the greater the amount of steam condensate required for abating the ammonia in the purge gas, through washing, downstream of the last condensation stage.

The amount of steam condensate required for washing also increases the higher the temperature of the cooling water becomes.

This flow of steam condensate requires oversizing of the water treatment section of the urea plant.

The larger the flow of water (or rather the water resulting from condensation of the steam used as the motive fluid in the ejectors of the vacuum system(s) and the steam condensate used for washing the purge gas) fed to the vacuum system(s) and subsequently to the water treatment section, the larger the flow of water that is recycled to the synthesis section together with the recovered reagents, with a consequent decrease in conversion by the synthesis reaction (an equilibrium reaction adversely affected by excess water).

In short, the problem with relatively large amounts of steam condensate is the necessity of oversizing the water treatment section, and a thermodynamic penalization of the urea synthesis reaction.

A further problem of vacuum systems of certain of the known art is that, due to the relatively high concentration of ammonia in the purge gas, it might be required (also according to local regulations in force) to send the current to a final treatment system before emission into the atmosphere. However, in a vacuum system of the above-described type, the purge gases are discharged into the atmosphere and there is insufficient pressure to transfer them to a final treatment system.

SUMMARY

An object of the present disclosure is to overcome certain of the above-mentioned drawbacks of certain of the known art; in particular, an object of the disclosure is to provide an apparatus and a method for the treatment of process vapours coming from a vacuum concentration section of a urea plant that has relatively improved efficiency with respect to certain of the known art.

The present disclosure therefore relates to an apparatus and a method for the treatment of process vapours coming from a vacuum concentration section of a urea plant, as defined in essential terms in the appended claims 1 and 13, respectively.

The disclosure provides an apparatus and a method that enable treating process vapours coming from a vacuum concentration section of a urea plant with relatively increased efficiency with respect to certain of the known art, in particular enabling a significant reduction of the amount of water required by a vacuum system serving a urea plant. In other terms, the disclosure provides an apparatus and a method capable of reducing the amount of steam condensate (i.e., water) necessary for the absorption of ammonia in vacuum systems serving urea plants. This result is primarily achieved through specific selection of the position and way of injecting the steam condensate in the vacuum system.

With respect to the normal solutions of certain of the known art, where the steam condensate is only injected in the washing column of the (incondensable) purge gas, and thus downstream of the vacuum system's condensation stages, in accordance with the disclosure the main (or, in certain instances, sole) point of injection of steam condensate (i.e., where the main or larger part (i.e., more than 50% by weight of the total amount of steam) condensate fed to the vacuum system, or possibly all of the steam condensate, is injected) is positioned upstream of at least one selected condensation stage of the vacuum system, in particular upstream of the second condensation stage. In this way, a significant reduction on the flow of steam condensate is achieved, indicatively in the order of 40%, with respect to certain of the systems of certain of the known art.

From the plant-engineering viewpoint, the injection of the steam condensate in that position can be implemented either by in-line injection of the steam condensate (i.e., on the line that connects the first condensation stage to the second condensation stage, but downstream of the steam ejector located along this line to not affect its operation), or by injecting the steam condensate directly inside the condenser of the second condensation stage (in particular through nozzles installable on the shell side of the heat exchanger defining said condenser, where vapour condensation takes place).

The disclosure also enables absorbing ammonia in a relatively more efficient manner with respect to the conventional configuration, because:

for the same temperature (and therefore the same Henry's law constant), a higher partial pressure of ammonia corresponds to higher absorption; and the heat of absorption of ammonia in water (exothermic chemical absorption) is dissipated inside the second condensation stage.

In accordance with another aspect of the disclosure, the amount of steam condensate necessary for the absorption of ammonia in the vacuum system is further reduced owing to a modification, with respect to configurations of certain of the known art, of the circuit of the cooling water fed to the vacuum system, aimed at reducing the temperature of the cooling water entering the individual condensers.

In particular, in accordance with the disclosure, the second condensation stage is fed directly with available cooling water at the relatively lowest temperature, instead of (as in certain of the known art) with cooling water coming from the heat exchangers (condensers) of the successive condensation stages.

Advantageously, the successive condensation stages are also fed with cooling water at the lowest available temperature.

In this way:

the total intake of water in the system is reduced, as the amount of steam necessary for the steam ejectors to perform the required pressure increase is reduced;

the amount of ammonia that can be absorbed increases, in particular at the second condensation stage, for the same thermal gradient ($\Delta T$) of approach on the relevant heat exchanger.

Advantageously, the cooling water is fed in parallel to the condensers of the second condensation stage and of the successive condensation stages (which are thus arranged according to a parallel configuration with respect to the cooling water).

Indicatively, for a reduction in the temperature of the cooling water of approximately 3° C., a further reduction in the flow of steam condensate in the order of 5% is obtained with respect to systems of the known art.

According to a further aspect of the disclosure, it is possible to increase the pressure of the purge gas (leaving the condensation stages) through the installation of a steam ejector downstream of the last condensation stage. In this way, the purge gas is given sufficient pressure to send it to a suitable treatment system.

Additional features are described in, and will be apparent from the following Detailed Description and the figures.

BRIEF DESCRIPTION OF THE DRAWINGS

Further characteristics and advantages of the present disclosure will become clearer from the description of the following non-limiting embodiments, referring to figures in the accompanying drawings, in which.

DETAILED DESCRIPTION

Figure 1:
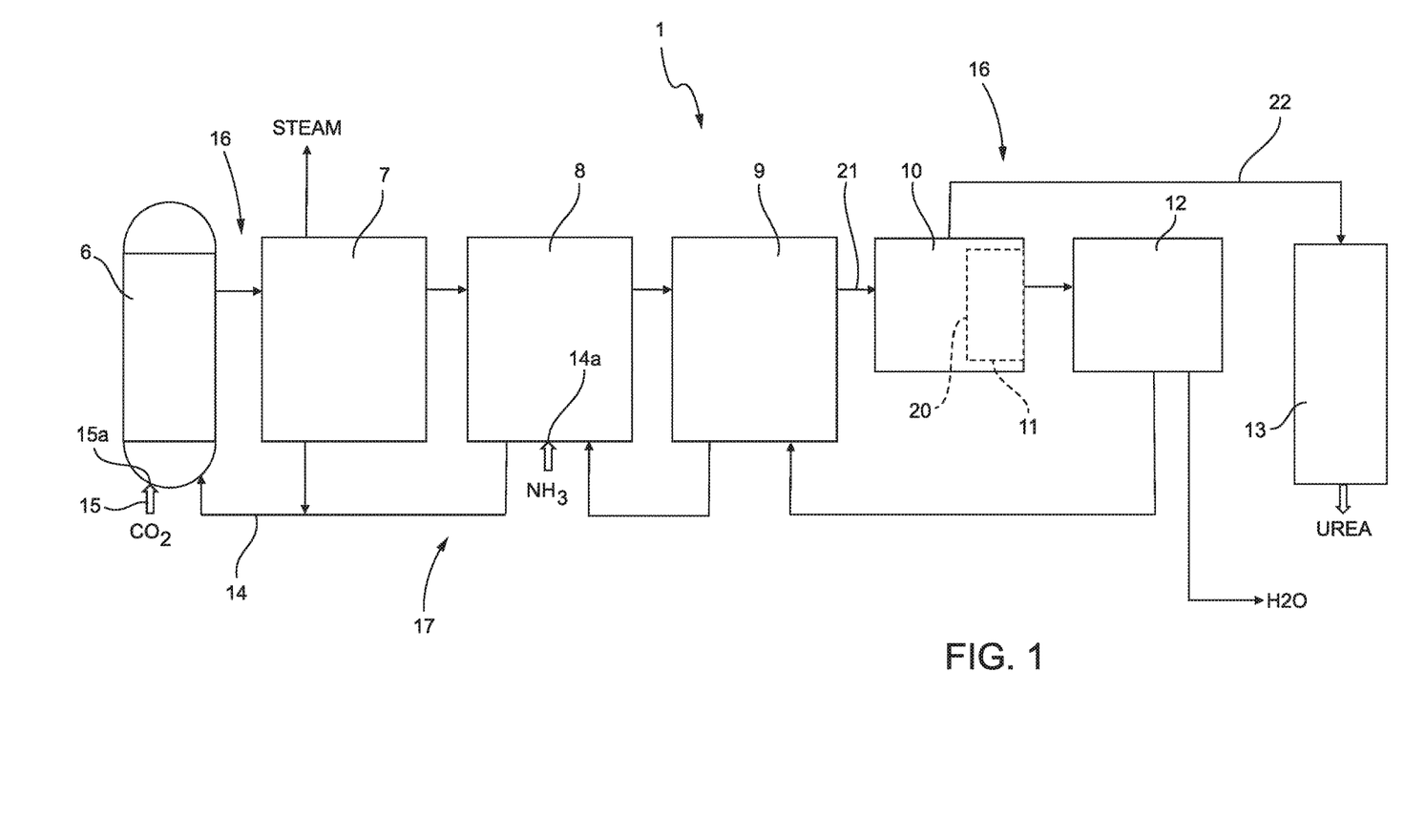
FIG. 1 is a schematic view of a urea production plant (urea plant) comprising a vacuum concentration section and an apparatus for the treatment of process vapours coming from the vacuum concentration section, in accordance with the disclosure.

FIG. 1 shows, in a relatively extremely schematic manner, a urea plant 1 (i.e., a plant for the production of urea).

The general configuration of the urea plant 1 can be of one of several types, as can the urea production process implemented in the plant.

Here, reference is made, purely by way of example, to a urea production plant/process according to the known "Snamprogetti" technology. It is understood that the disclosure is also applicable to other urea production plants/processes in which a vacuum concentration section or, in any case, at least one vacuum system is used.

In the non-limiting configuration shown, the urea plant 1 comprises, albeit not necessarily: a urea synthesis reactor 6 where a reaction of urea synthesis from ammonia and carbon dioxide takes place; recovery sections 7, 8 and 9, in particular a high-pressure recovery section 7, a medium-pressure recovery section 8 and a low-pressure recovery section 9, where a urea solution produced in the reactor 6 becomes progressively concentrated with the removal of unreacted ammonia and carbon dioxide and water, and the recovered components are recirculated; a vacuum concentration section 10 provided with a vacuum system 11; a process condensate treatment section 12; and a finishing/solidification section 13, comprising, for example, a granulator or prilling tower.

The reactor 6 is fed with NH3 and CO2 through respective feed lines 14 and 15, connected to respective inlets 14a and 15a from which NH3 and CO2 enter the urea plant 1. A urea circuit 16 gradually carries the urea solution produced in the reactor 6 away to the recovery sections 7, 8 and 9 and the vacuum concentration section 10, where the urea is progressively concentrated and separated from the unreacted reagents, before being sent to the finishing/solidification section 13. A recovery circuit 17 recirculates the unreacted reagents recovered by the recovery sections 7, 8 and 9 and by the process condensate treatment section 12 back to the reactor 6.

Not all of the components of the various sections and the circuits that connect them are indicated and described herein, but only those useful for understanding the present disclosure.

Figure 2:
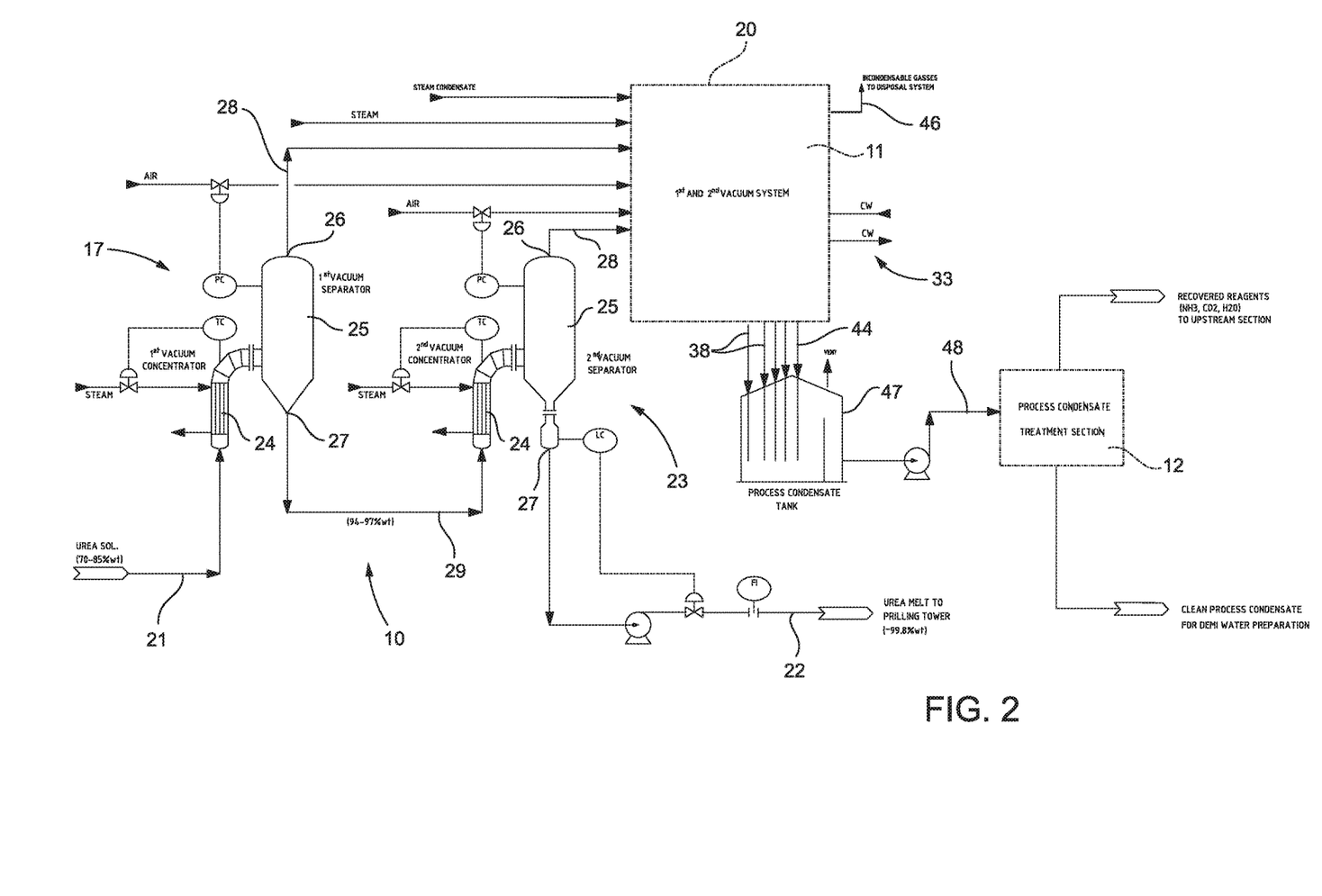
FIG. 2 is a schematic view in greater detail of the vacuum concentration section of the urea plant in FIG. 1 and integrating the apparatus in accordance with the disclosure.

Referring also to FIG. 2, the urea plant 1 comprises an apparatus 20 for the treatment of process vapours coming from the vacuum concentration section 10 and integrating the vacuum system 11.

The vacuum concentration section 10 is connected by a urea inlet line 21 and a urea outlet line 22 forming part of the urea circuit 16 to the low-pressure recovery section 9 and the finishing/solidification section 13, respectively.

The vacuum concentration section 10 comprises at least one concentration stage 23, connected to the vacuum system 11 of the apparatus 20 and operating in a vacuum to process (concentrate) the urea solution arriving from the low-pressure recovery section 9.

Again, depending on the type of finishing required for the product (granulated or prilled urea), the vacuum concentration section 10 may comprise several concentration stages 23 in series. For example, in the embodiment provided purely by way of example in FIG. 2, the vacuum concentration section 10 comprises two concentration stages 23.

Each concentration stage 23 can be configured in various ways. In the example shown, each concentration stage 23 comprises a concentrator 24 associated with a separator 25. For example, the concentrator 24 is a heat exchanger fed with steam (generated, in particular, by the high-pressure recovery section 7), and the separator 25 is a liquid-vapour phase separator connected to the concentrator 24.

The separator 25 has a top outlet 26 for the outflow of process vapours, and a bottom outlet 27 for the outflow of a concentrated urea solution.

The top outlet 26 is connected to the apparatus 20 through a vapour line 28; the bottom outlet 27 is connected to the finishing/solidification section 13 through the urea outlet line 22, or to the next concentration stage 23 (if several concentration stages 23 are provided) through a connecting line 29.

The vacuum system 11 ensures the vacuum conditions required in the respective concentration stage 23 (i.e., the operating pressure of the concentration stage 23 to which it is connected, through the condensation of the process vapours coming from the concentration stage 23).

If several concentration stages 23 are present, they are opportunely associated with respective vacuum systems 11. The apparatus 20 that treats the process vapours of the vacuum concentration section 10 therefore comprises one or more vacuum systems 11.

Figure 3:
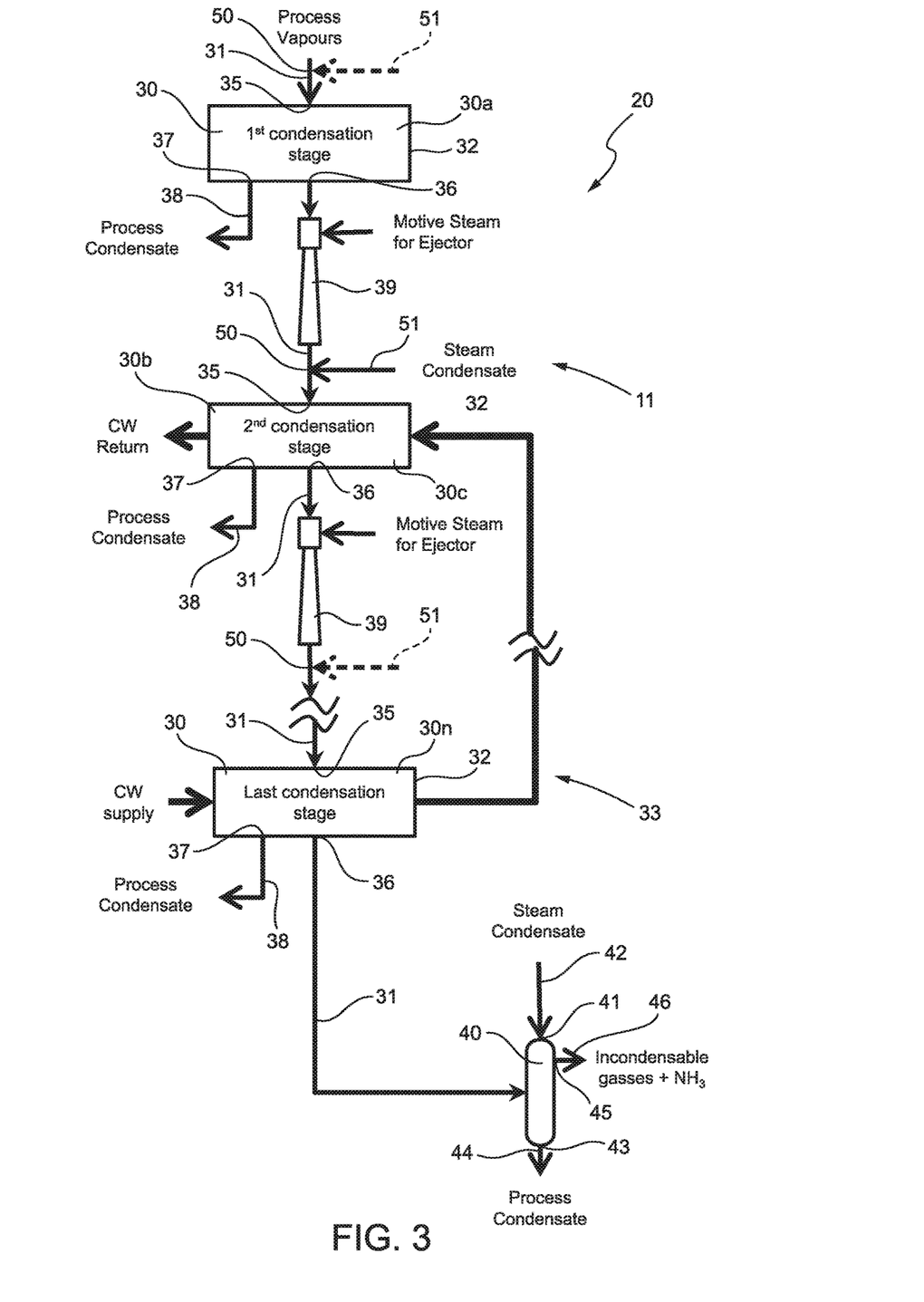
FIG. 3 is a schematic view of a first embodiment of the apparatus in accordance with the disclosure.

FIG. 3 shows a single vacuum system 11 forming part of the apparatus 20 of the disclosure.

The vacuum system 11 comprises a plurality of successive condensation stages 30 at increasing pressures, connected in series by respective line portions 31 and crossed in series by the process vapours to treat.

In particular, the vacuum system 11 comprises (in the order the process vapours pass through the vacuum system 11) a first condensation stage 30a and one or more further condensation stages 30b, including at least a second condensation stage 30c, up to a last condensation stage 30n.

For example, each condensation stage 30 is defined by a condenser 32, in particular constituted by a heat exchanger in which the flow of process vapours to treat transfers heat to a cooling fluid, for example cooling water.

In the example shown in FIG. 3, the cooling fluid (e.g., water) circulates in the condensation stages 30 in series, running through a cooling circuit 33 that connects the condensers 32 in series (in particular, the condensers 32 of the further condensation stages 30b, with exclusion of the first condensation stage 30a). The cooling fluid is first fed to the last condensation stage 30n and then in series to the further condensation stages 30b, with exclusion of the first condensation stage 30a.

Each condenser 32 (heat exchanger), defining a condensation stage 30, has an inlet 35 and an outlet 36 connected to respective line portions 31 for the inflow and outflow of process vapours, and a condensate outlet 37 connected to a condensate line 38, from which the process condensates that have condensed in the condenser 32 are recovered.

Each condensation stage 30 thus has an inlet 35 connected to a respective line portion 31 for feeding a flow of process vapours to be treated into the condensation stage 30, and an outlet 36 connected to a further respective line portion 31 for the outflow of process vapours treated in the condensation stage 30.

The condensers 32 (i.e., the respective condensation stages 30) are connected in series by the line portions 31 and operate at increasing pressure.

Each line portion 31 is provided with a pressure boost device 39, for example a steam ejector fed with steam (acting as the motive fluid), such as coming from the high-pressure recovery section 7. In the example shown in FIG. 3, the line portions 31 that connect together the further condensation stages 30b following the first condensation stage 30a are provided with respective pressure boost devices 39; it is understood that the line portion 31 that feeds the first condensation stage 30a could also be provided with a pressure boost device 39.

The pressure boost devices 39 are configured to increase the pressure of the flow of process vapours circulating in the line portions 31 from one condensation stage 30 to the next.

The outlet 36 of the last condensation stage 30n is connected to a washing unit 40 by a further line portion 31.

The washing unit 40 is, for example, a scrubber fed with steam condensate through an inlet 41 connected to a supply line 42.

The washing unit 40 has a condensate outlet 43 connected to a condensate line 44, from which the steam condensate used for washing is collected, and a gas outlet 45 connected to a discharge line 46, from which the remaining (incondensable) purge gases are collected, which are then sent to a specially provided discharge system (not shown).

The process condensates coming from each condensation stage 30 and from the washing unit 40 pass through the respective lines 38 and 44 and are transferred, possibly after being collected in a tank 47 (FIG. 2) optionally fitted with a vent, through a further condensate line 48 to the process condensate treatment section 12.

The vacuum system 11 of the apparatus 20 has at least one primary steam condensate inlet 50, connected by a steam condensate feed line 51 to a unit (not specifically shown; for example, located in the process condensate treatment section 12) of the urea plant 1 where steam condensate is produced (i.e., where the steam used in the urea plant 1 is condensed).

In particular, the primary inlet 50 defines the main injection point of the steam condensate in the vacuum system 11, intended as the point where the main or larger part (i.e., greater or equal to any other parts and/or greater or equal to 50% by weight), of all the steam condensate fed as a whole to the vacuum system 11 is injected.

In accordance with the disclosure, the primary inlet 50 is positioned upstream of at least one of the condensation stages 30 of the vacuum system 11, or in at least one of the condensation stages 30.

In the embodiment shown in FIG. 3, the selected condensation stage 30, fitted with the primary steam condensate inlet 50, is the second condensation stage 30c (always in the circulation direction of the process vapours in the vacuum system 11). In other words, the primary inlet 50 is positioned upstream of the second condensation stage 30c (always with reference to the circulation direction of the process vapours in the vacuum system 11), (i.e., between the first condensation stage 30a and the next (second) condensation stage 30c).

The primary inlet 50 can be positioned, for example, on the line portion 31 that connects the first condensation stage 30a to the second condensation stage 30c, downstream of the pressure boost device 39 (steam ejector) located along said line portion 31 (as shown by way of example in FIG. 3), or directly inside the condenser 32 of the second condensation stage 30c (being defined, for example, by one or more nozzles positioned on the shell side of the heat exchanger defining said condenser 32).

In other embodiments, schematically shown with broken lines in FIG. 3, instead of being positioned upstream of or inside the second condensation stage 30c, the primary inlet 50 is positioned upstream of or inside the first condensation stage 30a, or any one of the further condensation stages 30b.

In general, the primary inlet 50 can be positioned upstream of or inside any one of the condensation stages 30.

In other embodiments yet, the vacuum system 11 of the apparatus 20 has a plurality of primary steam condensate inlets 50, connected, for example, by respective steam condensate feed lines 51, to the steam condensate production unit and positioned upstream of respective condensation stages 30 of the vacuum system 11 and/or in respective condensation stages 30 (any two or more of the condensation stages 30, or even all the condensation stages 30).

Each primary inlet 50 can be positioned upstream of the respective condensation stage 30, on the line portion 31 that feeds steam condensate to the same condensation stage 30 and downstream of the pressure boost device 39 arranged along the same line portion 31, or inside the condenser 32 of the respective condensation stage 30.

The flow of steam condensate fed to each condensation stage 30 through the respective primary inlet 50 can be different depending on the position of the condensation stage 30 (in other words, the primary inlets 50 and the respective lines 51 are configured to supply the same or different flows of steam condensate to the respective condensation stages 30).

The main or larger part (i.e., greater or equal to any other parts and/or greater or equal to 50% by weight), of all the steam condensate fed as a whole to the vacuum system 11, is fed to the vacuum system 11 through the single primary inlet 50 or the plurality of primary inlets 50 as a whole.

In use, in implementation of the method in accordance with the disclosure, the apparatus 20 operates in the following manner.

The vacuum concentration section 10 receives an aqueous urea solution, also containing NH3 and CO2, through the urea inlet line 21 (FIG. 2).

The urea solution becomes concentrated in the vacuum concentration section 10, producing a flow of process vapours that is sent through the steam line 28 (or respective steam lines 28) to the apparatus 20 and precisely to the vacuum system 11 (or to respective vacuum systems 11).

In the vacuum system 11, the process vapours are treated in the condensation stages 30 in series: in each condensation stage 30, a process condensate is separated, which is collected through the condensate outlet 37 and sent to the process condensate treatment section 12 to recover the reagents, and a flow of uncondensed process vapours is passed to the next condensation stage 30.

A flow of (incondensable) purge gas exits from condensation stage 30n, which is washed in the washing unit 40 with steam condensate, supplied from inlet 41, to reduce NH3.

The process condensates collected from the various condensation stages 30, as well as those circulating in the vacuum system 11 and finally collected by the washing unit 40, are sent to the process condensate treatment section 12 to recover the reagents, which are recycled to the reactor 6.

Figure 4:
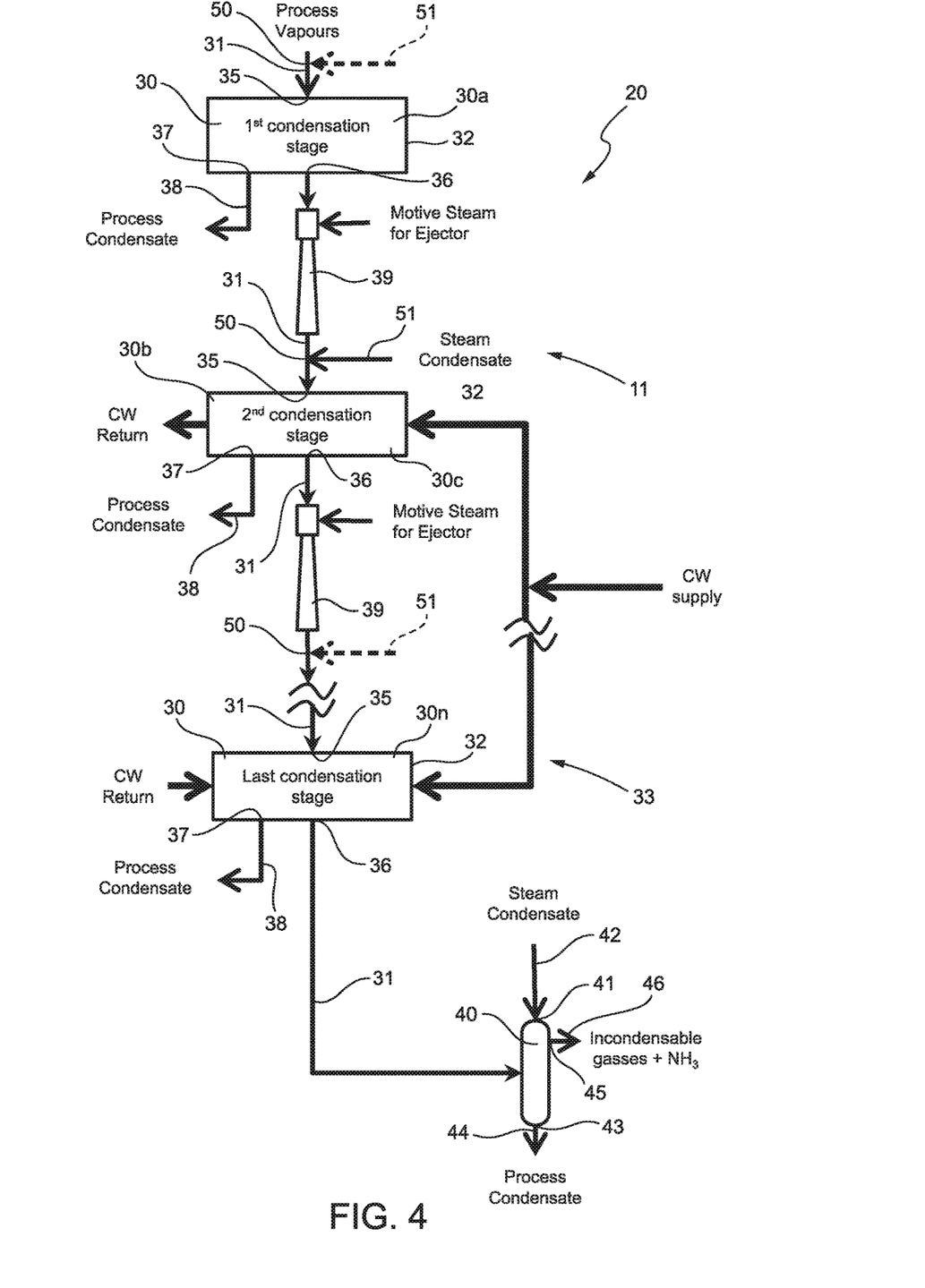
FIGS. 4 and 5 show further alternative embodiments of the apparatus of the disclosure.

In the embodiment in FIG. 4, where details similar or identical to those already described are indicated with the same reference numerals, the cooling fluid (e.g., water) circulates in the condensation stages 30 in parallel (instead of in series as shown in FIG. 3), running through the cooling circuit 33 that connects the condensers 32 in parallel with respect to the cooling fluid (in particular, the condensers 32 of the further condensation stages 30b, with exclusion of the first condensation stage 30a).

Figure 5:
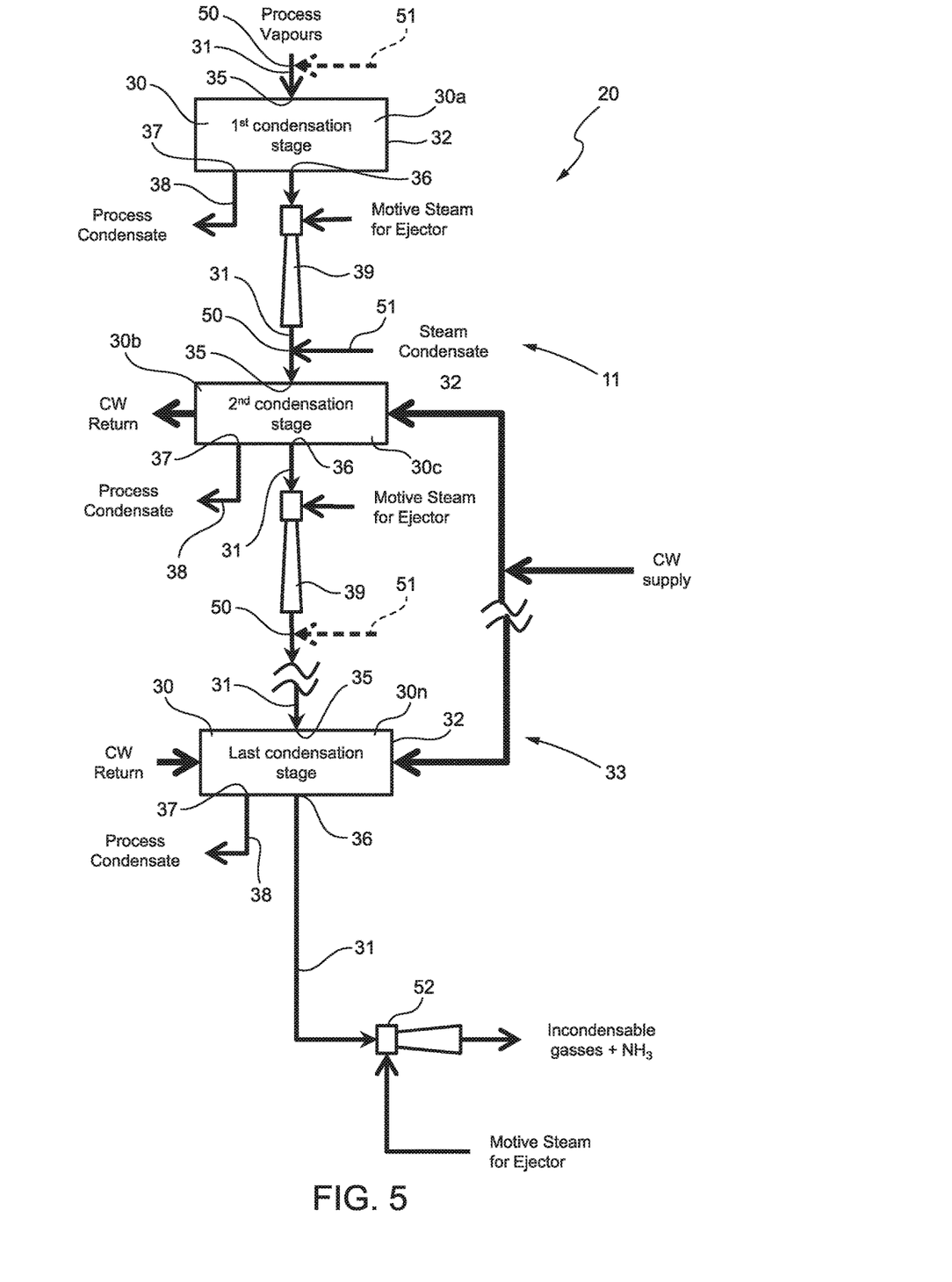

In the embodiment in FIG. 5, where details similar or identical to those already described are indicated with the same reference numerals, the vacuum system 11 is provided with a further final pressure boost device 52, in particular a steam ejector, located along the line portion 31 leaving the last condensation stage 30n, to increase the pressure of the purge gas leaving the vacuum system 11 to a suitable level to send said purge gas to a specific treatment unit (not shown).

It should be appreciated that in the embodiments in FIGS. 4 and 5, the apparatus 20 may comprise a single primary inlet 50, positioned upstream of or inside any one of the condensation stages 30, or a plurality of primary inlets 50, positioned upstream of or inside any respective condensation stages 30.

Finally, it is understood that further modifications and variants can be made regarding the apparatus and method described and illustrated herein without departing from the scope of the appended claims. Accordingly, various changes and modifications to the presently disclosed embodiments will be apparent to those skilled in the art.

The invention claimed is:

1. An apparatus comprising:
    a vacuum system having a plurality of successive condensation stages to treat, in series, process vapours, the plurality of successive condensation stages connected, in series, by a plurality of successive line portions;
    at least one primary steam condensate inlet that feeds steam condensate to the vacuum system, wherein the at least one primary steam condensate inlet defines a main injection point of steam condensate in the vacuum system where at least 50%, by weight, of all steam condensate is injected to the vacuum system and the at least one primary steam condensate inlet is arranged at at least one of: upstream, relative to a circulation direction of the process vapours through the vacuum system, of a selected one of the condensation stages, and in the selected one of the condensation stages; and
    a washing unit connected to a last one of the condensation stages by a last line portion of the plurality of successive line portions, the washing unit having:
        an inlet connected to a supply line fed with steam condensate,
        a condensate outlet connected to a condensate line from which steam condensate is used for washing is collectable, and
        a gas outlet connected to a discharge line from which incondensable purge gases are collectable.

2. The apparatus of claim 1, wherein:
    each condensation stage has an inlet connected to a respective one of the plurality of successive line portions that feeds the process vapours to treat; and
    the at least one primary steam condensate inlet is arranged on at least one of the line portions and downstream of a pressure boost device arranged along the line portion, the pressure boost device to increases a pressure of a flow of process vapours circulating in the line portion.

3. The apparatus of claim 1, wherein the at least one primary steam condensate inlet is positioned inside a condenser of the selected one of the condensation stages.

4. The apparatus of claim 1, wherein:
    the vacuum system comprises, in the circulation direction of the process vapours, a first condensation stage and at least one further condensation stage including at least one second condensation stage up to the last one of the condensation stages, and
    the at least one primary steam condensate inlet is positioned at one of:
        upstream of the at least one further condensation stage following the first condensation stage, and
        inside the at least one further condensation stage.

5. The apparatus of claim 4, wherein the selected one of the condensation stages is the second condensation stage in the circulation direction of the process vapours through the vacuum system.

6. The apparatus of claim 5, the at least one primary steam condensate inlet is positioned upstream of the second condensation stage, on the line portion connecting the first condensation stage to the second condensation stage and downstream of a pressure boost device arranged at one of: along the line portion connecting the first condensation stage to the second condensation stage and inside a condenser of the second condensation stage.

7. The apparatus of claim 1, further comprising a plurality of primary steam condensate inlets, wherein each primary steam condensate inlet is positioned at at least one of: upstream of a respective one of the condensation stages of the vacuum system and in a respective one of the condensation stages of the vacuum system.

8. The apparatus of claim 1, wherein:
    the condensation stages operate at increasing pressure, and
    each line portion connecting two successive condensation stages is coupled with a pressure boost device to increase a pressure of a flow of process vapours circulating in the line portion from one of the two successive condensation stages to the next of the two successive condensation stages.

9. The apparatus of claim 8, wherein the pressure boost devices comprise steam ejectors fed with steam acting as a motive fluid.

10. The apparatus of claim 1, wherein the condensation stages comprise respective condensers including respective heat exchangers in which a flow of process vapours to treat transfers heat to a cooling fluid circulating in a cooling circuit connecting, in parallel and with respect to the cooling fluid, at least two of the condensers.

11. The apparatus of claim 10, wherein the cooling circuit connects, in parallel, the condensers of a plurality of condensation stages following a first condensation stage which the flow of process vapours to treat first pass through.

12. The apparatus of claim 1, wherein the vacuum system comprises a pressure boost device positioned along the last line portion exiting from the last one of the condensation stages to increase a pressure of a flow of vent gas discharged from the vacuum system.

13. A method for treating process vapours coming from a vacuum concentration section of a urea plant, the method comprising:
  condensing the process vapours in a plurality of successive condensation stages, connected in series, of a vacuum system to create vacuum conditions in the vacuum concentration section positioned upstream of the condensation stages, wherein the vacuum system comprises the condensation stages and a washing unit connected to a last one of the condensation stages;
  supplying steam condensate at at least one main injection point where at least 50%, by weight, of all steam condensate is fed to the vacuum system, the at least one main injection point being positioned at at least one of: upstream, relative to a circulation direction of the process vapours through the vacuum system, of at least one selected condensation stage and inside the at least one selected condensation stage; and
  washing, in the washing unit, incondensable purge gas exiting from the last one of the condensation stages with steam condensate to reduce an amount of NH3.

14. The method of claim 13, further comprising increasing the pressure of a flow of process vapours upstream of the at least one selected condensation stage by a pressure boost device arranged upstream of the at least one selected condensation stage, wherein the main injection point is positioned downstream of the pressure boost device.

15. The method of claim 13, wherein the main injection point is positioned inside a condenser defining the at least one selected condensation stage.

16. The method of claim 13, wherein:
  the process vapours run through the condensation stages in a predetermined circulation direction, passing through a first condensation stage and then to at least one further condensation stage including at least a second of the condensation stages up to the last one of the condensation stages, and
  the main injection point is positioned at one of: a position upstream of one of the further condensation stages following the first condensation stage, and a position inside one of the further condensation stages.

17. The method of claim 16, wherein the main injection point is positioned at one of: a position upstream the second condensation stage and a position inside the second condensation stage.

18. The method of claim 13, further comprising suppling steam condensate at a plurality of injection points, wherein each injection point is positioned, with respect to the circulation direction of the process vapours in the vacuum system, upstream of a respective one of the condensation stages and inside a respective one of the condensation stages.

19. The method of claim 13, further comprising increasing a pressure of a flow of process vapours between each condensation stage and the next, if any, condensation stage.

20. The method of claim 19, wherein the pressure rise is obtained by steam ejectors fed with steam as a motive fluid.

21. The method of claim 13, wherein in said condensation stages, heat is transferred from the process vapours by heat exchange with a cooling fluid which is fed in parallel to at least one of the condensation stages.

22. The method of claim 21, wherein the cooling fluid is fed in parallel to a plurality of condensation stages following a first condensation stage that the process vapours first pass through.

23. The method of claim 13, further comprising increasing a pressure of a flow of vent gas exiting from the last one of the condensation stages by a steam ejector.

24. A system comprising:
  a vacuum concentration section, and
  an apparatus to treat process vapours coming from the vacuum concentration section, the apparatus comprising:
    a vacuum system having a plurality of successive condensation stages to treat, in series, the process vapours, the plurality of successive condensation stages connected in series by a plurality of successive line portions;
    at least one primary steam condensate inlet that feeds steam condensate to the vacuum system, wherein the at least one primary steam condensate inlet defines a main injection point of steam condensate in the vacuum system where at least 50%, by weight, of all steam condensate is injected to the vacuum system and the at least one primary steam condensate inlet is arranged at at least one of: upstream, relative to a circulation direction of the process vapours through the vacuum system, of a selected one of the condensation stages, and in the selected one of the condensation stages; and
    a washing unit connected to a last one of the condensation stages by a last line portion of the plurality of successive line portions, the washing unit having:
      an inlet connected to a supply line fed with steam condensate,
      a condensate outlet connected to a condensate line from which steam condensate is used for washing is collectable, and
      a gas outlet connected to a discharge line from which incondensable purge gases are collectable.

* * * * *